(12) United States Patent
Moribe et al.

(10) Patent No.: US 7,773,213 B2
(45) Date of Patent: Aug. 10, 2010

(54) OPTICAL EXTERIOR INSPECTION APPARATUS AND METHOD

(75) Inventors: Hideyuki Moribe, Tokyo (JP); Takeshi Bashomatsu, Tokyo (JP)

(73) Assignee: NEC Corporation, Tokyo (JP)

( * ) Notice: Subject to any disclaimer, the term of this patent is extended or adjusted under 35 U.S.C. 154(b) by 0 days.

(21) Appl. No.: 12/426,562

(22) Filed: Apr. 20, 2009

(65) Prior Publication Data

US 2009/0262340 A1  Oct. 22, 2009

(30) Foreign Application Priority Data

Apr. 21, 2008  (JP) ............................ P2008-110550

(51) Int. Cl.
*G01N 21/00* (2006.01)
*G01N 21/88* (2006.01)

(52) U.S. Cl. ................................ 356/237.4; 356/237.3

(58) Field of Classification Search ... 356/237.1–237.6, 356/239.1–239.8, 124, 124.5; 250/306, 307, 250/310, 227.27
See application file for complete search history.

(56) References Cited

U.S. PATENT DOCUMENTS

| | | | | |
|---|---|---|---|---|
| 3,585,847 A * | 6/1971 | Brenden | ....................... | 73/605 |
| 3,586,444 A * | 6/1971 | Sproul et al. | ................. | 356/129 |
| 3,879,989 A * | 4/1975 | Brenden | ....................... | 73/605 |
| 3,983,529 A * | 9/1976 | Langlois | ....................... | 367/10 |
| 4,379,408 A * | 4/1983 | Sandhu | ......................... | 73/603 |
| 4,906,083 A * | 3/1990 | Sattler | .......................... | 359/386 |
| 5,445,011 A * | 8/1995 | Ghislain et al. | ............... | 73/105 |
| 5,825,043 A * | 10/1998 | Suwa | .......................... | 250/548 |
| 6,407,385 B1 * | 6/2002 | Okada | ........................... | 850/3 |
| 6,449,049 B1 * | 9/2002 | Lam et al. | .................... | 356/515 |
| 6,654,110 B2 * | 11/2003 | Yonezawa et al. | ......... | 356/237.2 |
| 7,599,545 B2 * | 10/2009 | Shibata et al. | ............... | 382/141 |
| 2009/0168191 A1 * | 7/2009 | Takehisa et al. | ............. | 359/665 |

FOREIGN PATENT DOCUMENTS

JP   1998185531 A   7/1998

* cited by examiner

*Primary Examiner*—Sang Nguyen

(57) ABSTRACT

An inspected object (e.g., a reticle) is stored in an immersion cassette filled with a liquid having a specific refraction factor. An inspection beam is irradiated toward the inspected object, which is subjected to precise positioning, via an objective lens while being refracted by the liquid, thus producing a reflected inspection beam reflected by the inspected object and a transmitted inspection beam transmitted through the inspected object. Image processing is performed based on at least one of the reflected inspection beam and the transmitted inspection beam, thus producing an inspected image of the inspected object. The inspected image is compared with a prescribed circuit pattern so as to inspect the existence and nonexistence of foreign matter or structural defects on the exterior of the inspected object. Thus, it is possible to secure an adequate focal depth of the objective lens while achieving a high resolution in imaging the inspected object.

6 Claims, 4 Drawing Sheets

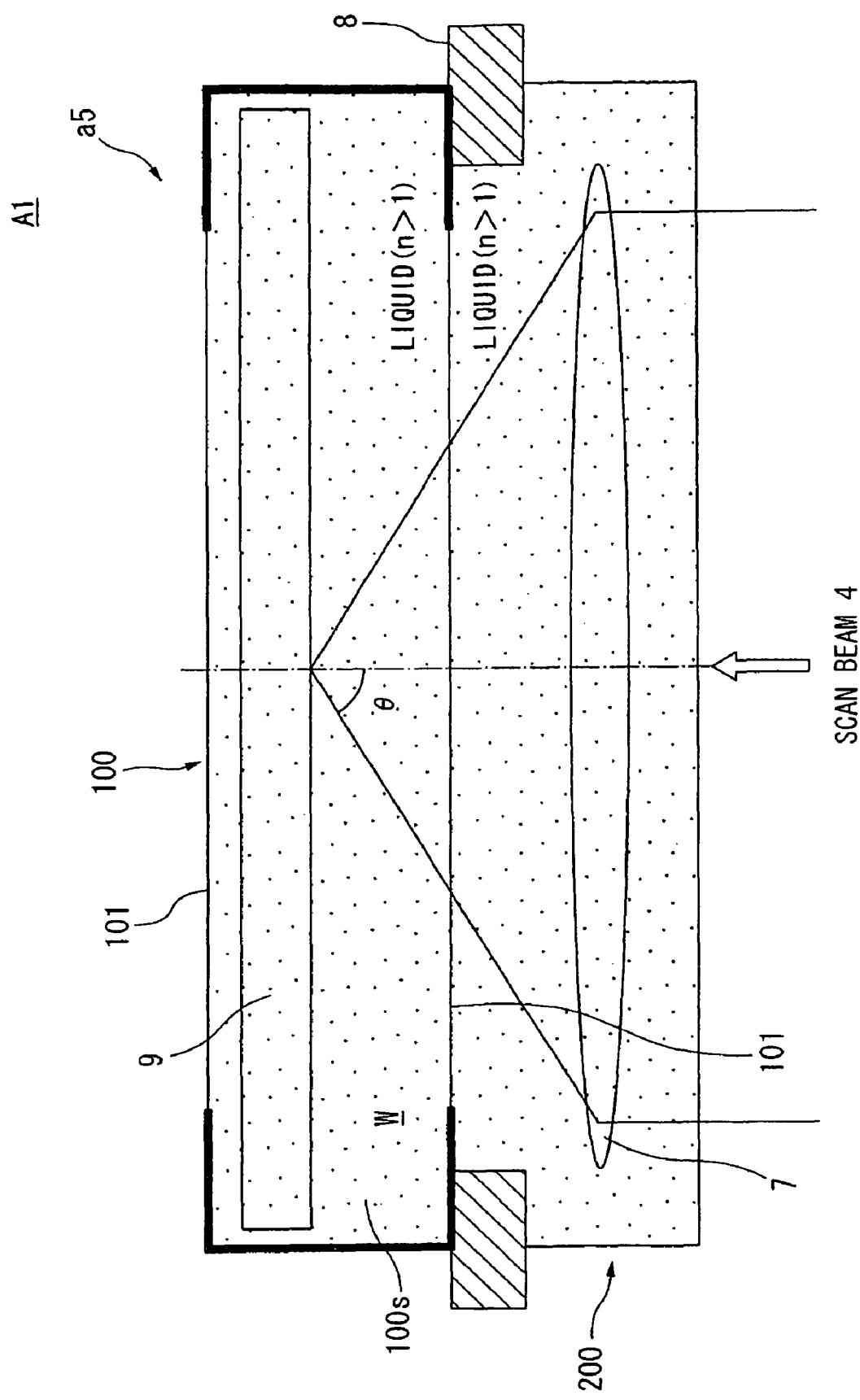

OPTICAL EXTERIOR INSPECTION APPARATUS AND METHOD

BACKGROUND OF THE INVENTION

The present application claims priority from Japanese Patent Application No. 2008-110550 filed Apr. 21, 2008, the content of which is incorporated herein by reference.

FIELD OF THE INVENTION

The present invention relates to optical exterior inspection apparatuses and methods, which inspect the existence or nonexistence of foreign matter attached to or defects on masks having fine structures, in particular onto reticles used for photographing patterns of semiconductor integrated circuits.

DESCRIPTION OF THE RELATED ART

Due to recent advancement in highly-integrated semiconductor elements, reticles serving as circuit patterns of semiconductor elements have been progressing in terms of fine structure. Accordingly, optical inspection apparatuses, which inspect the existence or nonexistence of foreign matter or structural defects on reticles, should progress in terms of high resolution.

Generally, the resolution of an optical inspection apparatus is inversely proportional to the wavelength of a light source producing an inspection beam and is proportional to the numerical aperture (NA) of an objective lens positioned proximate to an inspected object; hence, the conventionally-known technology achieves high-resolution inspection by reducing the wavelength of a light source or by increasing the numerical aperture. Various technologies have been developed and disclosed in various documents such as Patent Document 1.

Patent Document 1: Japanese Unexamined Patent Application Publication No. H10-185531

Patent Document 1 teaches an exterior inspection apparatus for a high-resolution pattern, in which ultraviolet light having a relatively short wavelength of 363.8 nm is used to achieve high-resolution inspection and to improve defective inspection precision.

Compared to reducing the wavelength of light as taught in Patent Document 1, it is easy to increase the numerical aperture of an objective lens in high-resolution inspection; however, a high numerical aperture reduces focal depth. For example, when the numerical aperture becomes higher than 0.8, the focal depth must be greatly reduced and thereby fall within the range of 0.1 µm to 0.3 µm, whereby it becomes difficult to control a focal point. Even when using an inspection apparatus having an objective lens of a high numerical aperture, it is very difficult to precisely detect foreign matter or defects on a reticle due to errors occurring in controlling the focal point.

SUMMARY

The invention seeks to solve the above problem, or to improve upon the problem at least in part.

In one embodiment, there is provided an optical exterior inspection apparatus that includes an inspection beam irradiation unit for irradiating an inspection beam toward an inspected object (e.g., a reticle), a positioning unit for establishing the prescribed positioning of the inspected object relative to the inspection beam, a light reception unit for receiving at least one of a reflected inspection beam reflected by the inspected object and a transmitted inspection beam transmitted through the inspected object, an image processor for performing image processing based on at least one of the reflected inspection beam and the transmitted inspection beam, and a liquid immersion unit for storing the inspected object therein, which is filled with a liquid so as to refract the inspection beam irradiated toward the inspected object.

In another embodiment, there is provided an optical exterior inspection method in which an inspection beam is irradiated toward an inspected object which is stored in a liquid, so that image processing is performed based on at least one of a reflected inspection beam reflected by the inspected object and a transmitted inspection beam transmitted through the inspected object, thus inspecting the exterior of the inspected object.

The present invention demonstrates the following effects.

(1) Since the inspection beam is refracted in the liquid and is then incident on the inspected object, the numerical aperture of an objective lens, by which the inspection beam converges on the inspected object, increases by the refraction factor n of the liquid (where the refraction factor of air is "1") while the resolution decreases by the factor 1/n. This indicates that an incident angle of the inspection beam on the inspected object decreases by the factor 1/n while the focal depth increases by the factor n when the resolution is constant. Thus, it is possible to secure an adequate focal depth while maintaining a high resolution.

(2) By use of the liquid immersion unit having a transparent window for introducing the inspection beam toward the inspected object, it is possible to avoid contamination of the inspection beam irradiation unit which is positioned without contact with the liquid.

(3) By use of a detachable container serving as the liquid immersion unit, it is possible to physically separate the liquid immersion unit from the inspection beam irradiation unit and the positioning unit. This simplifies the overall constitution of the optical exterior inspection apparatus while avoiding variations of the refraction factor of the liquid due to the occurrence of flowing. In addition, it is possible to improve the maintainability.

(4) By use of a liquid-filler filled with a liquid medium and positioned between the inspection beam irradiation unit and the liquid immersion unit, it is possible to refract the inspection beam multiple times. By changing the refraction factor of the liquid medium from the refraction factor of the liquid of the liquid immersion unit, it is possible to improve the degree of freedom in designing optics including an objective lens by which the inspection beam converges on the inspected object. In addition, it is possible to reliably avoid the contamination of the inspection beam irradiation unit.

BRIEF DESCRIPTION OF THE DRAWINGS

The above features and advantages of the present invention will be more apparent from the following description of certain preferred embodiments taken in conjunction with the accompanying drawings, in which:

FIG. 4 is an illustration showing a modified example of the reticle inspection apparatus.

DETAILED DESCRIPTION OF PREFERRED EMBODIMENT

The present invention will be now described herein with reference to illustrative embodiments. Those skilled in the art will recognize that many alternative embodiments can be accomplished using the teachings of the present invention and that the invention is not limited to the embodiments illustrated for explanatory purposes.

Figure 1:
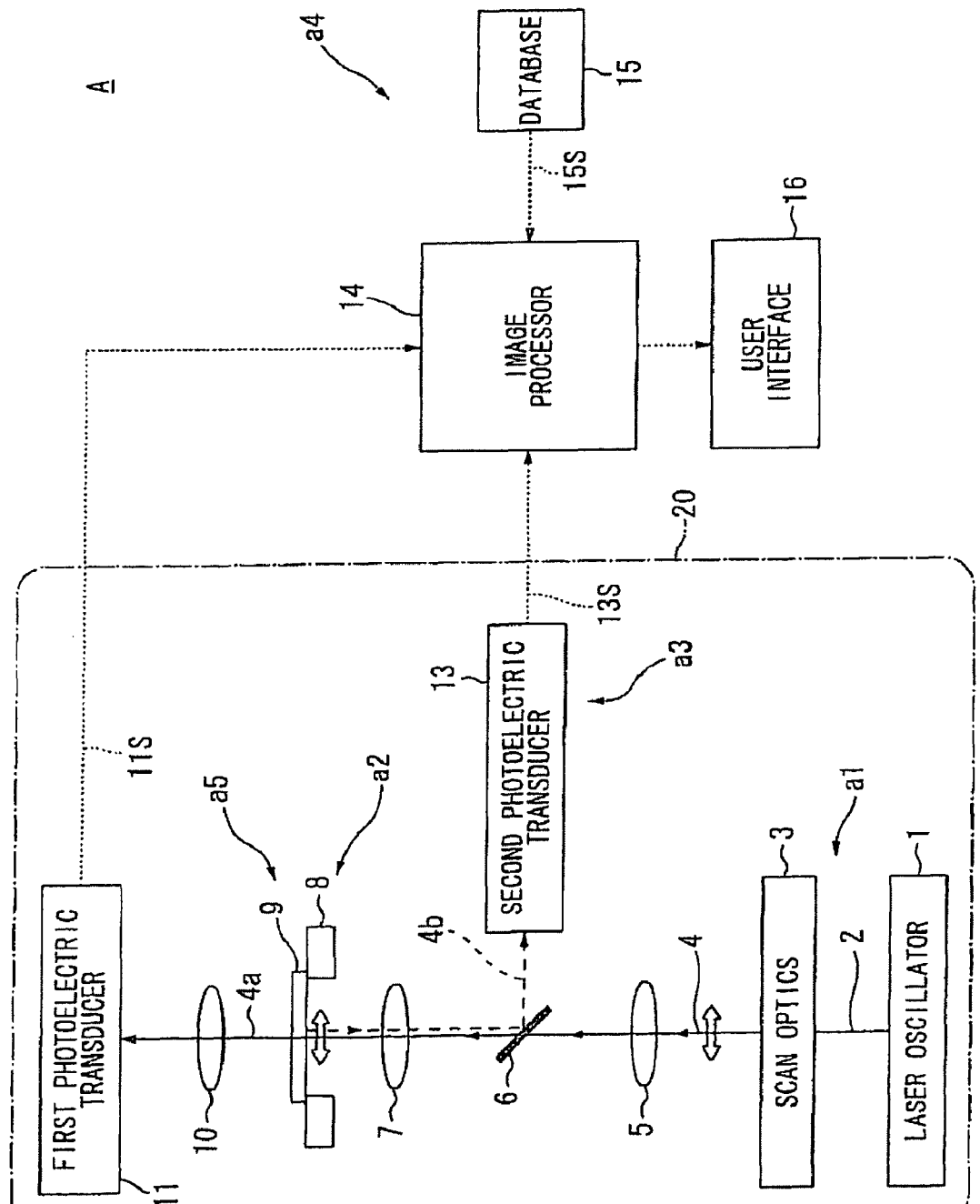
FIG. 1 is a block diagram showing the constitution of an optical exterior inspection apparatus (i.e., a reticle inspection apparatus) in accordance with a preferred embodiment of the present invention.

FIG. 1 is a block diagram showing the constitution of an optical exterior inspection apparatus (i.e., a reticle inspection apparatus A), in accordance with a preferred embodiment of the present invention. The reticle inspection apparatus A includes an inspection beam irradiation unit a1, a positioning unit a2, a beam reception unit a3, an image inspection unit a4, and a liquid immersion unit a5.

The inspection beam irradiation unit a1 irradiates an inspection beam to a reticle 9 (i.e., an inspected object), wherein it includes a laser oscillator 1, a scan optics 3, a propagation optics 5, and an objective lens 7.

The laser oscillator 1 serves as a light source of a laser beam 2, which adopts a far ultraviolet ray of a 266 nm-wavelength in order to improve a resolution.

The scan optics 3 scans the laser beam 2 irradiated by the laser oscillator 1, wherein it uses an acoustic-optical device (AOD), a galvano-mirror, a polygon mirror, or the like.

The propagation optics 5 propagates a scan beam (or an inspection beam) 4 scanned by the scan optics 3. The present embodiment adopts a synthetic-quarts lens, which is optimal for transmitting far ultraviolet light therethrough, as the propagation optics 5.

The objective lens 7 achieves convergence on a small spot which is smaller than the scan beam 4 propagating through the propagation optics 5. The present embodiment adopts the objective lens 7 of NA=0.8. In this connection, it is preferable to use an objective lens whose NA is 0.8 or more in order to achieve sufficient convergence of the scan beam 4.

The positioning unit a2 composed of a stage 8 establishes a prescribed positioning of the reticle 9 relative to the scan beam 4 irradiated by the inspection beam irradiation unit a1. The stage 8 moves the reticle 9 relative to the objective lens 7 so that a laser beam will be irradiated at a prescribed portion of the reticle 9.

The light reception unit a3 includes a half-mirror 6, a collector lens 10, a first photoelectric transducer 11, and a second photoelectric transducer 13.

The half-mirror 6 is positioned between the propagation optics 5 and the objective lens 7 so as to extract a reflected scan beam 4b, which is reflected by the reticle 9, from the scan beam 4 irradiated by the inspection beam irradiation unit a1. It is possible to substitute a polarized beam splitter for the half-mirror 6. Herein, it is preferable to modify the constitution in such a way that a linear polarized beam is controlled using a wavelength plate in polarization, thus improving a beam splitting efficiency.

A transmitted scan beam 4a transmitted through the reticle 9 converges at the collector lens 10, which adopts a high numerical aperture.

The first photoelectric transducer 11 detects an optical intensity of the transmitted scan beam 4a so as to produce an electric signal 11S, while the second photoelectric transducer 13 detects an optical intensity of the reflected scan beam 4b so as to produce an electric signal 13S. The electric signals 11S and 13S are supplied to the image inspection unit a4. It is preferable for the photoelectric transducers 11 and 13 to operate with high response and capability of detecting subtle light, wherein it is possible to use photo-diodes, for example.

The reticle inspection apparatus A is equipped with an optical scanner 20 including the inspection beam irradiation unit a1, the positioning unit a2, and the light reception unit a3.

The image inspection unit a4 includes an image processor 14, which performs image processing using the electric signals 11S and 13S so as to perform a comparison based on circuit pattern data 15S, a database 15 storing the circuit pattern data 15S, and a user interface 16 which is used to display an inspection result and to perform various operations.

Figure 2:
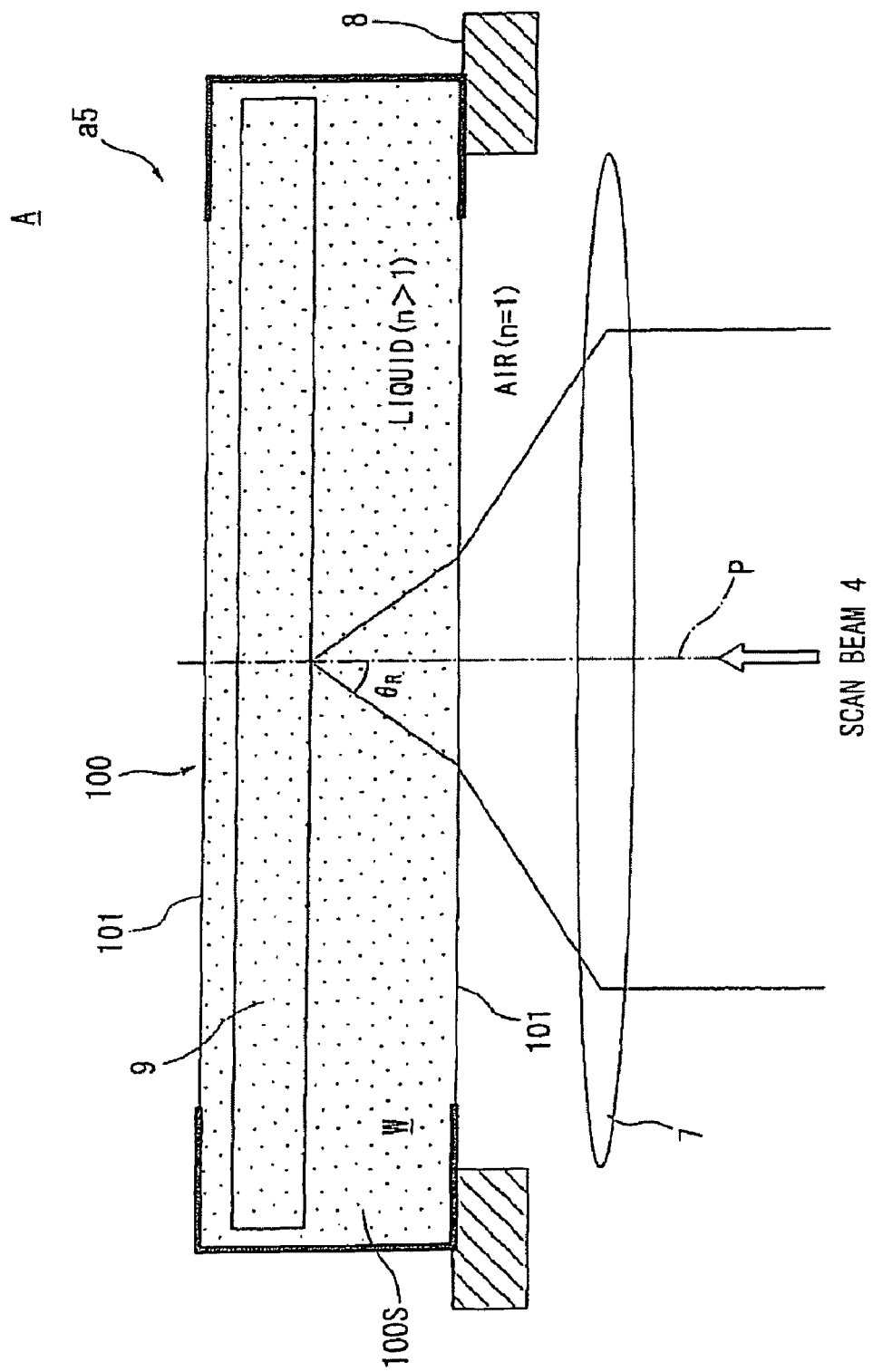
FIG. 2 is an illustration showing a liquid immersion unit and its periphery for applying a scan beam to a reticle held inside an immersion cassette in association with the reticle inspection apparatus.

FIG. 2 shows a liquid immersion unit a5 and its periphery.

The liquid immersion unit a5 includes an immersion cassette 100 serving as a storage space 100S for storing the reticle 9 and containing pure water W therein. That is, the reticle 9 immersed in the pure water W is fixed inside the immersion cassette 100.

The immersion cassette 100 has a window 101 for transmitting the scan beam 4 therethrough. The window 101 introduces the scan beam 4 irradiated by the inspection beam irradiation unit a1 into the storage space 100S of the immersion cassette 100.

The immersion cassette 100 is arranged independently of the inspection beam irradiation unit a1 and the positioning unit a2 and is detachably attached to the stage 8. As shown in FIG. 2, positioning the immersion cassette 100 relative to the stage 8 automatically establishes the positioning of the reticle 9 with respect to the laser beam 2.

Next, the operation of the reticle inspection apparatus A having the above constitution will be described with reference to FIGS. 1 and 2. The following description will be given with respect to the outline operation of the reticle inspection apparatus A first, and then, with respect to the characteristics of the reticle inspection apparatus A.

First, the outline operation of the reticle inspection apparatus A will be described below.

In FIG. 1, the laser beam 2 irradiated by the laser oscillator 1 is scanned by the scan optics 3 and is then converted into the scan beam 4. The transmitted scan beam 4a is changed so as to have a desired beam diameter and a desired scan width, and then transmits through the half-mirror 6 (or a polarized beam splitter). Then, the transmitted scan beam 4a converges on the reticle 9 installed in the immersion cassette 100 by way of the objective lens 7.

Thereafter, the transmitted scan beam 4a further transmitted through the reticle 9 converges on the collector lens 10 and is then incident on the first photoelectric transducer 11. Based on the optical intensity of the transmitted scan beam 4a, the first photoelectric transducer 11 produces and outputs the electric signal 11S to the image processor 14. The reflected scan beam 4b is split by the half-mirror 6 and is then supplied to the second photoelectric transducer 13, which in turn produces and outputs the electric signal 13S to the image processor 14.

The image processor 14 performs image processing based on the electric signals 11S and 13S so as to produce an inspected image. Then, the image processor 14 compares the inspected image representing the circuit pattern of the reticle 9 with the circuit pattern data 15S given by the database 15 so as to detect defects by way of Die-DB inspection. Instead of Die-DB inspection, it is possible to perform Die-Die inspection for comparing real images.

Figure 3:
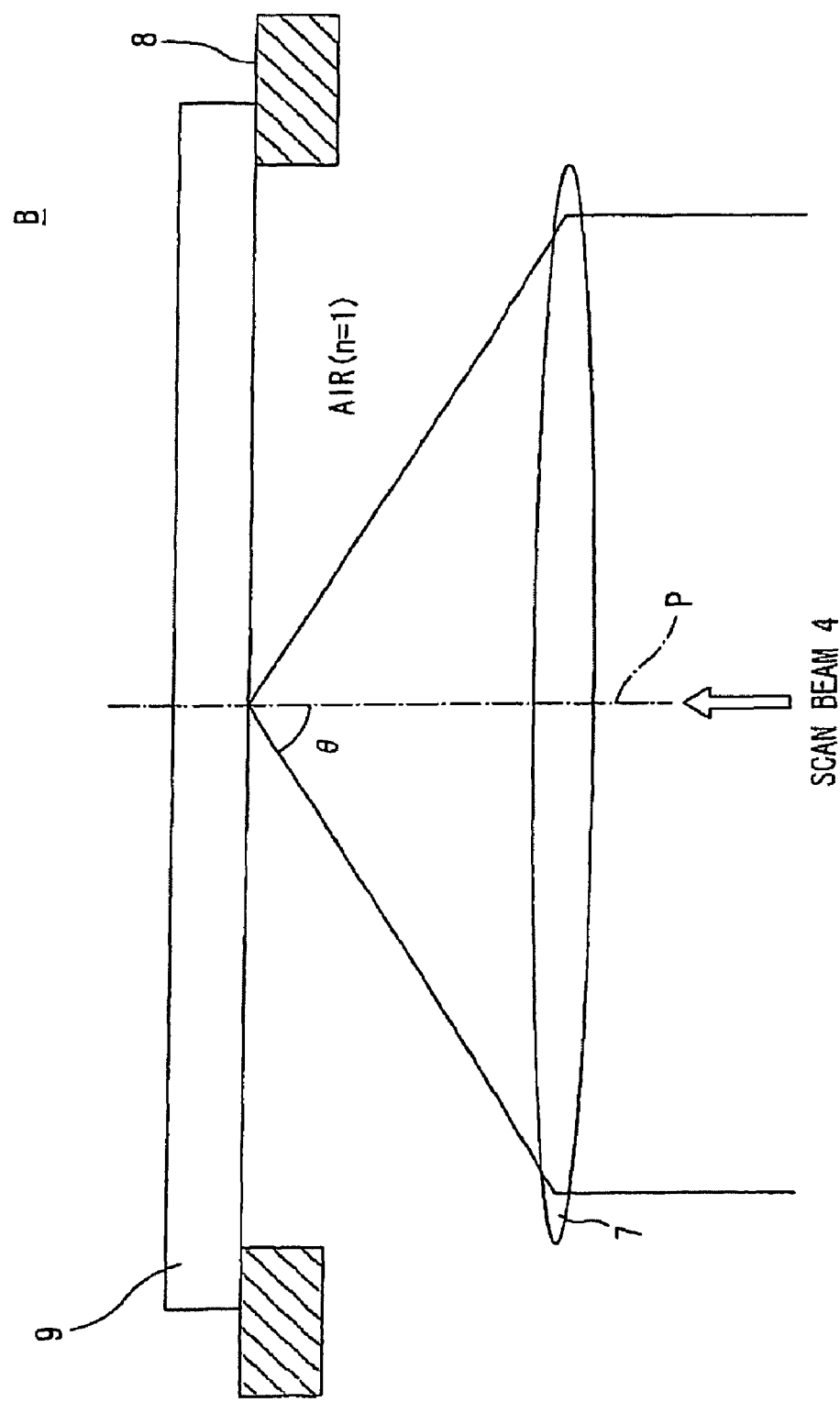
FIG. 3 is an illustration showing a foregoing reticle inspection apparatus for inspecting the reticle.

Next, the characteristics of the reticle inspection apparatus A will be described with reference to FIG. 2 in comparison with FIG. 3 showing the characteristics of a foregoing reticle inspection apparatus B.

In the foregoing reticle inspection apparatus B shown in FIG. 3, the scan beam 4 converges on the objective lens 7 with an angle θ and is then directly incident on the reticle 9 which is held in the air. In the reticle inspection apparatus A shown in FIG. 2 in which the reticle 9 is immersed in the pure water W in the immersion cassette 100, the scan beam 4 converging on the objective lens 7 with the angle θ is refracted by the pure water W and is then incident on the reticle 9 with a refracted angle $θ_R$ (where $θ_R < θ$).

Generally, the relationship between the numerical aperture (NA) of an objective lens and a refraction factor n is given by relational expression (1).

$$NA = n \times \sin θ \quad (1)$$

In the relational expression (1), θ designates an angle between incidence light (corresponding to the scan beam 4) and an optical axis P. The relationship between a resolution ε and a wavelength λ of an inspection beam as well as the numerical aperture (NA) of an objective lens is given by relational expression (2).

$$ε = k \times λ / NA \quad (2)$$

In the relational expression (2), k designates a constant dependent upon optics.

The relational expression (1) indicates that NA increases by the factor n as the refraction factor n of a medium becomes higher than n=1 when the angle θ is constant. The relational expression (2) indicates that the resolution ε becomes smaller as NA becomes higher when the wavelength λ is constant, wherein the resolution ε decreases by the factor 1/n.

As described above, it is possible to increase the focal depth while increasing the resolution by use of the liquid immersion.

In the reticle inspection apparatus A shown in FIG. 2, an air gap (where n=1) lies between the objective lens 7 and the window 101 of the immersion cassette 100, while the pure water W (where n>1) lies between the reticle 9 and the window 101 of the immersion cassette 100. Due to a critical angle of full reflection, the upper limit of the numerical aperture (where NA<1) of the objective lens 7 remains the same between the reticle inspection apparatuses A and B shown in FIGS. 2 and 3, the resolution E does not change between them. This indicates that the reticle inspection apparatus A is capable of increasing the focal depth. Similar to the refraction factor of the pure water W, the refraction factor of the window 101 is greater than "1" (where n>1); hence, the same result can be obtained from both of the reticle inspection apparatuses A and B.

Since the reticle inspection apparatus A is designed to incorporate only the reticle 9 into the immersion cassette 100, which is detachably attached thereto, it is unnecessary to arrange a new immersion-specified device; hence, the existing system can be easily modified to cope with liquid immersion by introducing a simple optics for correcting an optical aberration occurring due to liquid immersion in the immersion cassette 100.

Since the reticle inspection apparatus A allows the immersion cassette 100 to be detached therefrom and subjected to maintenance, it is possible to improve operability and maintainability.

Due to the scanning method, no flow occurs in the pure water W even when the stage 8 normally moves for the purpose of photographing the reticle 9; hence, it is possible to avoid variations of the refraction factor, variations of optics, degradation of the resolution, and unwanted deviations of the image quality.

Since the objective lens 7 is not brought into direct contact with the pure water W, it is possible to avoid the contamination of the objective lens 7.

The present embodiment shows an illustrative example in terms of procedures, shapes of parts, and combinations of parts; hence, it can be modified in various ways based on design requirements or the like.

FIG. 4 shows a reticle inspection apparatus A1 according to a modified example of the present embodiment, in which parts identical to those of the reticle inspection apparatus A are designated by the same reference numerals.

The reticle inspection apparatus A1 is equipped with a liquid-filler 200 filled with a liquid medium, which is positioned to contain the objective lens 7 in proximity to the window 101 of the immersion cassette 100. That is, two liquid media are arranged in connection with the window 101; hence, it is possible to avoid contamination of the objective lens 7 and to set different refraction factors with respect to two liquid media. This yields a certain degree of freedom in designing the objective lens 7. It is noticed that the total optics of the reticle inspection apparatus A1 including the objective lens 7 should be designed to cope with liquid immersion.

The present invention is not necessarily limited to reticle inspection apparatuses for inspecting the existence and non-existence of foreign matter and structural defects on reticles. The present invention is applicable to other types of optical inspection apparatuses for inspecting MEMS parts and electronic devices with fine structures.

The liquid immersion unit a5 is not necessarily designed to use the pure water W but can be redesigned to use other liquid media.

In the present embodiment, the stage 8 normally moves to scan the reticle 9; but this is not a restriction. That is, the stage 8 can be driven in units of steps.

The light reception unit a3 is not necessarily equipped with both of the first photoelectric transducer 11 and the second photoelectric transducer 13. For the purpose of only inspecting structural defects, it is sufficient to produce an inspected image of the reticle 9 based on the reflected scan beam 4b. For the purpose of only inspecting foreign matter attached to the reticle 9, it is sufficient to produce an inspected image of the reticle 9 based on the transmitted scan beam 4a.

Lastly, it is apparent that the present invention is not limited to the above embodiment and variations, but may be further modified and changed without departing from the scope or spirit of the invention.

What is claimed is:

1. An optical exterior inspection apparatus comprising:
   an inspection beam irradiation unit for irradiating an inspection beam toward an inspected object;
   a positioning unit for establishing prescribed positioning of the inspected object relative to the inspection beam;
   a light reception unit for receiving at least one of a reflected inspection beam reflected by the inspected object and a transmitted inspection beam transmitted through the inspected object;
   an image processor for performing image processing based on the at least one of the reflected inspection beam and the transmitted inspection beam;
   a liquid immersion unit for storing the inspected object therein, wherein the liquid immersion unit is to be filled with a liquid so as to refract the inspection beam irradiated toward the inspected object, the liquid having a refraction factor greater than one; and, an objective lens through which the inspection beam is to be irradiated from the inspection beam irradiation unit toward the inspected object, the objective lens having a numerical aperture of at least 0.8, wherein the objective lens is positioned so that the inspection beam is to pass through the liquid that is to refract the inspection beam and then is to converge on the inspected object at a predetermined angle, and wherein the numerical aperture of the objective lens is equal to the refraction factor of the liquid multiplied by a sine of the predetermined angle.

2. The optical exterior inspection apparatus according to claim 1, wherein the liquid immersion unit is equipped with a transparent window for introducing the inspection beam.

3. The optical exterior inspection apparatus according to claim 1, wherein the liquid immersion unit is a detachable container containing the inspected object and filled with the liquid.

4. The optical exterior inspection apparatus according to claim 1 further comprising a liquid-filler which is filled with a liquid medium and is positioned between the inspection beam irradiation unit and the liquid immersion unit so as to preliminary refract the inspection beam incident on the liquid immersion unit.

5. An optical exterior inspection method comprising:

irradiating an inspection beam toward an inspected object which is stored in a liquid through an objective lens having a numerical aperture of at least 0.8, the liquid having a refraction factor greater than one;

receiving at least one of a reflected inspection beam reflected by the inspected object and a transmitted inspection beam transmitted through the inspected object; and performing image processing, by a processing device, based on the at least one of the reflected inspection beam and the transmitted inspection beam, to inspect an exterior of the inspected object to locate whether any foreign matter is attached to the inspected object, wherein the objective lens is positioned so that the inspection beam passes through the liquid that refracts the inspection beam and then converges on the inspected object at a predetermined angle, and wherein the numerical aperture of the objective lens is equal to the refraction factor of the liquid multiplied by a sine of the predetermined angle.

6. An optical exterior inspection apparatus using image processing, comprising:

a liquid immersion unit to immerse an inspected object within a liquid having a refraction factor greater than one; and, an objective lens having a numerical aperture of at least 0.8, the objective lens being precisely positioned so that a scan beam transmitted therethrough is to converge on the inspected object via the liquid being refracted, wherein the objective lens is positioned so that the scan beam is to pass through the liquid that is to refract the scan beam and then is to converge on the inspected object at a predetermined angle, and wherein the numerical aperture of the objective lens is equal to the refraction factor of the liquid multiplied by a sine of the predetermined angle.

* * * * *